United States Patent [19]

Tham et al.

[11] Patent Number: 5,701,888
[45] Date of Patent: Dec. 30, 1997

[54] AUTOMATIC AIR WASH FOR ANESTHESIA SYSTEM

[75] Inventors: Robert Q. Tham; Todd Keitel, both of Dane County, Wis.

[73] Assignee: Ohmeda Inc., Liberty Corner, N.J.

[21] Appl. No.: 692,248

[22] Filed: Aug. 5, 1996

[51] Int. Cl.$^6$ .................................................. A61M 16/00
[52] U.S. Cl. ........................... 128/204.21; 128/204.22; 128/204.23; 128/205.11; 128/203.12
[58] Field of Search ................. 128/202.22, 203.13, 128/203.14, 204.22, 205.11, 205.23, 204.21, 204.23, 204.25, 204.28, 205.12, 205.28, 203.12

[56] References Cited

U.S. PATENT DOCUMENTS

| | | | |
|---|---|---|---|
| 4,127,121 | 11/1978 | Westenskow et al. | 128/203.14 |
| 4,150,670 | 4/1979 | Jewett et al. | 128/204.22 |
| 4,203,434 | 5/1980 | Brooks | 128/205.24 |
| 4,345,612 | 8/1982 | Koni et al. | 128/204.21 |
| 4,602,653 | 7/1986 | Ruiz-Vela et al. | 128/205.11 |
| 4,878,388 | 11/1989 | Loughlin et al. | 128/205.11 |
| 4,883,051 | 11/1989 | Westenskow et al. | 128/204.21 |
| 4,971,049 | 11/1990 | Rotariu et al. | 128/204.26 |
| 5,293,866 | 3/1994 | Padula | 128/205.23 |

FOREIGN PATENT DOCUMENTS

| | | | |
|---|---|---|---|
| 2176313 | 12/1986 | United Kingdom | 128/203.12 |

*Primary Examiner*—Vincent Millin
*Assistant Examiner*—V. Srivastava
*Attorney, Agent, or Firm*—Roger M. Rathbun; Salvatore P. Pace

[57] ABSTRACT

An anesthesia system is disclosed that prolongs the lifetime of an oxygen fuel cell be used to detect the concentration of oxygen in that anesthesia system. The system determines and provides a signal indicating the end of any particular operation using the anesthesia system and that signal is used to cut off all gas supplies with the exception of the fresh air supply which is then allowed to pass through the system to wash the various lines, including the conduit having the oxygen gas fuel cell thus preventing the typically high concentrations of oxygen used in a operation from remaining in the oxygen fuel cell for an unnecessary period of time. Furthermore, the gases in the anesthesia machine are eliminated along with their deleterious effects and replaced by fresh air from the normal supply of fresh air to the system.

13 Claims, 1 Drawing Sheet

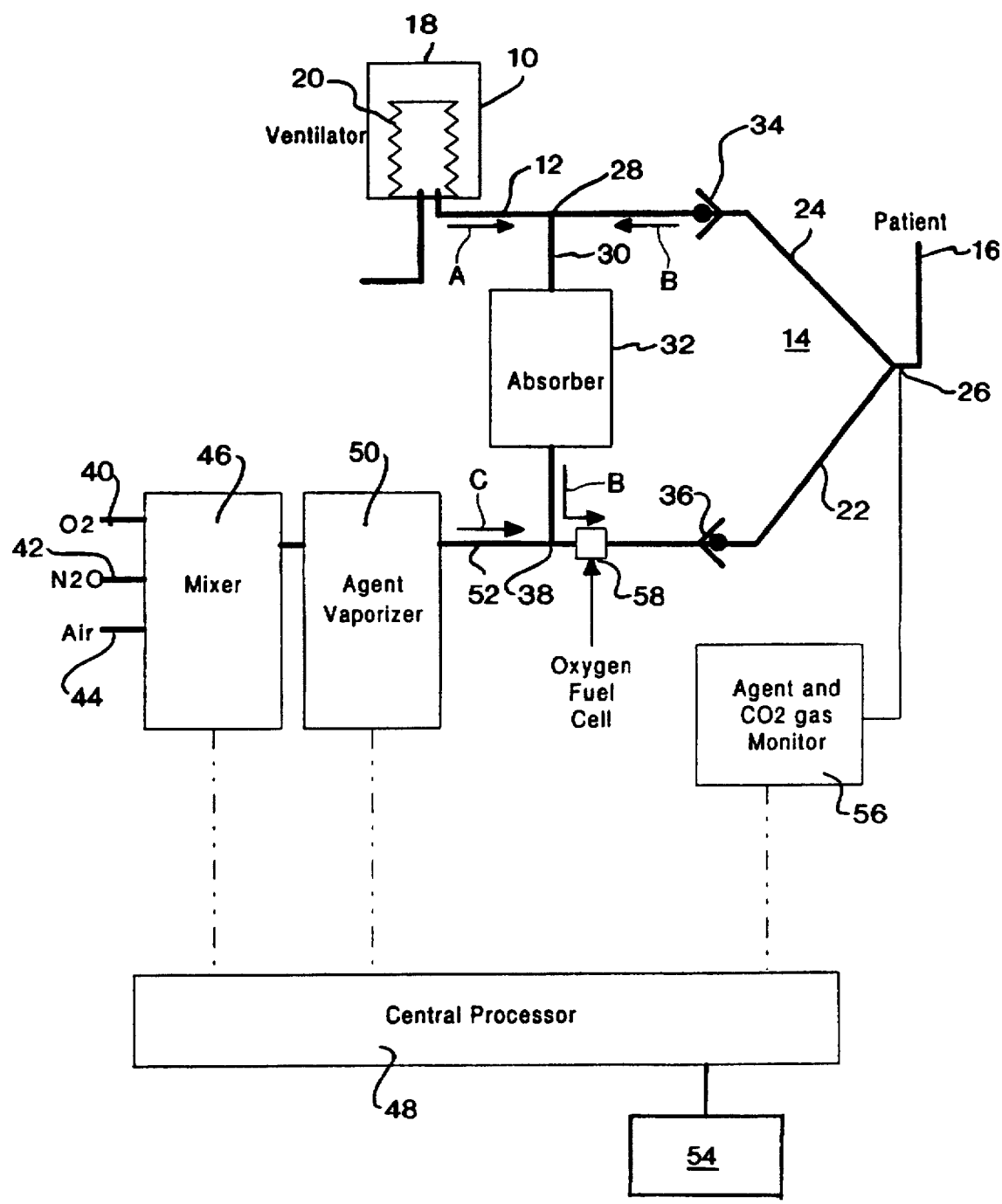

AUTOMATIC AIR WASH FOR ANESTHESIA SYSTEM

BACKGROUND OF THE INVENTION

The present invention relates to anesthesia systems used to provide an anesthetic agent to a patient undergoing an operation.

In general, anesthesia systems are utilized in operating rooms and comprise various equipment necessary to anesthetize the patient and maintain the patient in that state until the operation is completed and it is possible to terminate the introduction of the anesthetic agent.

Such systems comprise various pressure regulators, flow control devices, gas mixing devices and vaporizers to vaporize a volatile liquid anesthetic and to introduce the anesthetic laden gases into the patient. The patient is connected to the system by means of a face mask or other device and which interfaces with the anesthesia system via a patient circuit that may typically have an inspiratory limb through which the gases are introduced into the patient and an expiratory limb that conveys the exhaled gases from the patient.

In a typical anesthesia system, the overall flow of gases to and from the patient are generally of a high oxygen concentration and upon the termination of the medical procedure, those gases remain in the anesthesia system for a period of time.

One of the difficulties of allowing such gases to remain in the anesthesia system is that such systems typically employ oxygen fuel cells to sense the oxygen in the system and the continued presence of a high oxygen atmosphere will reduce the life of the cell. As a further problem, some anesthetics have an adverse reaction in the presence of soda lime, the substance used in medical absorbers in anesthesia systems and therefore the continued presence of the anesthetic agent within the absorber is also undesirable.

SUMMARY OF THE INVENTION

The anesthesia system of the present invention includes a means of detecting the termination of the use of the anesthesia machine of a medical operation and then stopping the flow of all gases through the system and purging the system with the fresh air from the supply of air.

The means of determining the end of the medical operation maybe by a number of signals. Included in such determination can be by the user turning the machine to standby following an operation, by the user declaring the end of an anesthetic case by an input means, detecting a signal when the patient is disconnected from the machine or a further variety of signals that let the machine central processing unit know that the operation has ended and the anesthesia machine is finished its use for that particular patient.

Upon recognition of that signal indicating the operation has terminated, the central processing unit (CPU) controlling the introduction and mixing of the various gases signals the gas valves to turn off the supplies to all of the gases and anesthetic agent with the exception of air. The air is then allowed to flow through the system at a predetermined flow rate to wash the anesthesia machine of the gases remaining in the various conduits and components, including purging the oxygen rich gas from the conduit where the oxygen cell is located.

The CPU may include a timing means that will then terminate the air flow when sufficient time has elapsed to assure that all of the affected passages contain only air or, alternatively, the normal oxygen sensor can be used as an input to the CPU and the flow of air discontinued when the oxygen concentration is reduced to about 21 percent, thereby indicating that air is present in the conduits of the anesthesia system. Alternatively, the flow of air can be terminated when the concentration of anesthetic agent in the patient circuit is reduced to less than 0.2% by volume. In either instance, the clinician is assured that the relative passages of the anesthesia system have been sufficiently washed so as to protect the $O_2$ sensor and to prevent the other aforementioned difficulties.

Other objects, features and advantages of the present invention will be more apparent from the detailed description of the preferred embodiments set forth below, taken in conjunction with the accompanying drawings.

BRIEF DESCRIPTION OF THE DRAWINGS

The FIGURE is a block diagram of the components of an anesthesia system used to carry out the present invention.

DESCRIPTION OF THE PREFERRED EMBODIMENT

Referring now to the FIGURE, there is shown a block diagram of an anesthesia system adapted to carry out the subject invention. As shown, a ventilator 10 is provided and which may be of the type shown and described in U.S. Pat. No. 5,315,989 assigned to the present applicant and the disclosure of which is incorporated herein by reference. That ventilator 10 of the aforementioned U.S. Patent has an inhalation cycle and an exhalation cycle controlled by a CPU.

The ventilator 10 provides gas to the patient during the inhalation cycle via a conduit 12 to the patient breathing circuit 14 where it is delivered to the patient 16. The ventilator 10 typically includes a bellows assembly 18 and air or other powering gas is supplied to the bellows assembly 18 exterior of the bellows 20 and which then collapses the bellows 20 to force gases within the bellows 20 to the patient 16. As shown in the FIGURE, a circle type of patient breathing circuit 14 is shown, however, it will be understood that various other circuit configurations can be used with the present invention including an open circuit or a Mapleson type circuit.

As also noted in the aforementioned U.S. Patent, the patient breathing circuit 14 itself conventionally includes an inspiratory limb 22 and an expiratory limb 24 and the patient is connected to a wye connection 26 located intermediate the inspiratory and the expiratory limbs 22,24. The means of connection may be an endotracheal tube, face mask or other interface between the patient 16 and the patient breathing circuit 14.

In conventional operation, gas is delivered to the patient 16 by means of a powering gas that collapses the bellows 20 to drive the gas into conduit 12 and then into the tee 28 where the gas enters a conduit 30 and passes through an absorber 32. After passing through the absorber 32, the gas enters the inspiratory limb 22 of the patient breathing circuit 14 to be administered to the patient 16. As the patient exhales, that exhalation, now laden with $CO_2$, passes through the expiratory limb 24 where it again passes through the tee 28 and continues to the absorber 32 where the $CO_2$ is eliminated by a $CO_2$ absorbing material, such as sodalime. Removal of the $CO_2$ by the soda lime releases water into the absorber 32.

A pair of check valves 34 and 36 are positioned in the patient breathing circuit 14 in the expiratory and inspiratory limbs 24 and 22, respectively, to maintain the flow of gas in the proper direction around the circle patient breathing circuit 14.

A flow of fresh gas is also introduced into the patient breathing circuit 14 and, as shown, is added at a tee 38 and thus into the inspiratory limb 22 of the patient breathing circuit 14. That flow of fresh gas is provided from a source of gas, typically oxygen and air, and may include nitrous oxide to aid in anesthetizing the patient. As shown in the FIGURE, there is a supply of oxygen 40, nitrous oxide 42 and air 44 and such supply may be through a central piping system of a hospital or may be through the use of individual cylinders of such gases.

In any event, the gases are mixed in a gas mixer 46 in the proportion desired by the user. The actual control of the proportions and the flow through the gas mixer 46 is, in the preferred embodiment, controlled by a central processing unit (CPU) 48. The mixed gases from the gas mixer 46 then pass through an agent vaporizer 50 where liquid anesthetic agent is vaporized and added to the stream of gas such that anesthetic laden gas continues into a conduit 52 and enters the patient breathing circuit 14 at the tee 38.

Again, in the preferred embodiment, the control of the agent vaporizer 50 is by means of the CPU 48 and which determines the percentage concentration of anesthetic agent that is in the gas that enters the patient breathing circuit 14 and thus that is supplied to the patient to induce and maintain anesthesia.

The CPU 48 is, in turn, controlled by an input device 54 provided so that the clinician can input the data needed to determine the various parameters to provide the flow and anesthetic concentration desired to anesthetize the patient.

In the overall flow scheme of the present conventional system, the gas is forced by the ventilator 10 into conduit 12 in accordance with the arrow A during the inhalation cycle of the patient 16. That air thus passes through the tee 28 and through absorber 32 where it further passes through tee 38 and into the inspiratory limb 22 of the patient breathing circuit 14. At that tee 38, fresh gas containing a predetermined concentration of an anesthetic agent is joined with the gases from the ventilator and proceeds with the gases already circulating in patient breathing circuit 14 and administered to the patient 16.

When the patient exhales, the exhaled gases pass through the expiratory limb 24 of the patient breathing circuit 14 through tee 28 and continue through the circuit, passing though the absorber 32 where the gases are scrubbed to eliminate the $CO_2$ that is exhaled by the patient 16.

As can be seen, therefore, the anesthesia system is basically a circle system where the gases continue to pass in a circle as shown by the arrows B with the addition of fresh gas and the anesthetic agent added to those gases in the direction of Arrow C as the gases pass around the circle portion of the circle system.

As a further component of the overall anesthesia system a gas monitor 56 is provided to detect the gases in the patient wye connection 26 and thus determine the actual gases that are introduced into the patient 16. Such gas analyzers conventionally detect nitrous oxide, carbon dioxide and the anesthetic agent being used in the particular system.

Also, an oxygen fuel cell 58 is conventionally provided in the anesthesia system and which specifically detects and monitors the oxygen concentration in the inspiratory limb 22 of the patient breathing circuit 14. Due to the nature of such fuel cells, a voltage is generated in accordance with the amount of oxygen in the passageway and thus, for so long as that oxygen is present, the fuel cell 58 continues to operate and to provide a signal.

In carrying out the anesthesia of a patient, typically, the oxygen concentration of the gases provided to the patient is of a high oxygen concentration, generally about 30% and thus the fuel cell will put out a signal representative of that high value and its lifetime shortened by the amount of time that signal is being generated. At the final stages of the anesthesia case, typically, 100% oxygen is washed into the patient to build up a reserve of oxygen in preparation for extubation and to wash the inhaled anesthetic agent out of the patient for emergence from anesthesia.

Frequently, after the use of the anesthesia system has been terminated, that is the particular operation is over and the patient disconnected, the inspiratory limb 22, as well as the other of the various gas containing conduits in the anesthesia system are still filled with a gas having an oxygen concentration of almost 100 percent. In addition, moisture from the expired gases and the product of the $CO_2$ absorption leaves the breathing circuit with high humidity.

In the case of a relatively high oxygen concentration, obviously, the continued period of time that the fuel cell 58 is exposed to the gases shortens the life time of the fuel cell 58. Since the replacement of the fuel cell 58, while not complicated, is an annoyance and the fuel cells themselves an unwanted expense, any action to prolong the life of the fuel cell 58 is advantageous.

In addition, the high humidity has a deleterious effect in that it is a good atmosphere for the growth of microbes in the system, again, a potentially harmful effect. Further, the continued presence of an anesthetic agent in the absorber 32 can cause problems with the breakdown of he anesthetic agent via some reaction with the absorbent material used in the absorber 32.

Accordingly, in accordance with the present invention, a signal source 60 is provided to the system that informs the CPU 48 that the particular operation has been terminated and that the anesthesia system is no longer being used in carrying out the anesthesia of a patient. The signal source may be from a variety of sensors, that is, the signal may be from the shut off switch or standby switch on the anesthesia machine and which indicates the termination of use of the anesthesia system. Alternatively, the signal source may be sent via the input device 54 when the user declares the end of an anesthesia case.

In any event, a signal is provided to the CPU 48 indicating the termination of an operation and that the anesthesia system is not being used further. The CPU thus sends a signal to the gas mixer 46 and instructs the gas mixer 46 to turn off the oxygen supply 40 and the nitrous supply 42, if either of those supplies are still on, and opens the flow of air from the air supply 44 to wash the system, and, in particular, the inspiratory limb 22 where the oxygen fuel cell 58 is present. By the flow of air, the various conduits are washed of the high humidity, high oxygen concentration gases and the overall system is filled with air.

The flow of air can continue until it is assured that the various anesthesia gases are fully washed from the system and all of the conduits. That flow may be terminated by a timer that is established at a predetermined time to assure the flow is sufficient or, alternatively, the gas monitor 56 can be utilized to continue to monitor the constituents of the gases within the inspiratory limb 22 and terminate the air wash when the concentration of oxygen falls below a predetermined concentration, for example, less that 21% indicating that the oxygen level is reaching the normal level of oxygen in air. As a further alternative, the gas monitor 56 may monitor the concentration of anesthetic agent and discontinue the air wash when the agent concentration in the patient wye connection 26 has been reduced to a predetermined amount, for example less than 0.2% by volume.

In any instance, the CPU 48 determines that the appropriate conduits of the anesthesia system have been sufficiently washed of the gases used during anesthesia and replaced with air, thus promoting the lifetime of the oxygen fuel cell as well as preventing the other deleterious effect those gases have on the anesthesia system.

While the present invention has been set forth in terms of a specific embodiment, it will be understood that the anesthesia system herein disclosed may be modified or altered by the those skilled in the art to other configurations. Accordingly, the invention is to be broadly construed and limited only by the scope and spirit of the claims appended hereto.

We claim:

1. An anesthesia system for providing anesthesia to a patient, the combination comprising;

a patient circuit adapted to be connected to the patient, said patient circuit introducing gases into the patient and for receiving gases exhaled by the patient, means to introduce a plurality of gases, including at least fresh air and oxygen, at a controllable flow into the patient circuit, an oxygen fuel cell in said patient circuit monitoring the concentration of oxygen in the patient circuit and generating a signal indicative of the oxygen concentration, means to generate a signal indicating the termination of the use of the anesthesia system on the patient; and means responsive to said signal to provide a flow of only said fresh air to wash said oxygen fuel cell.

2. An anesthesia system as defined in claim 1 wherein said means responsive to said signal to provide a flow of said fresh air includes a timing means and wherein said timing means terminates the flow of said fresh air upon the passage of a predetermined time period.

3. An anesthesia system as defined claim 1 wherein said means responsive to said signal to provide a flow of said fresh air terminates said flow when the oxygen concentration detected by said oxygen fuel cell is reduced to a predetermined concentration.

4. An anesthesia system as defined in claim 3 wherein said predetermined concentration is about 21 percent of oxygen.

5. An anesthesia system for providing anesthesia to a patient, the combination comprising;

a patient circuit adapted to be connected to the patient, said patient circuit introducing gases into the patient and for receiving gases exhaled by the patient, means to introduce a plurality of gases, including at least fresh air and oxygen into said patient circuit, control means to control the flow of each of said gases into said patient circuit, an oxygen fuel cell in said patient circuit monitoring the concentration of oxygen in the patient circuit and generating a signal indicative of the oxygen concentration, means to transmit a signal to said control means indicating the termination of the use of the anesthesia system on the patient; and said control means receiving said signal and increasing the flow of air to said patient circuit while terminating the flow of all of said other plurality of gases to said patient circuit to provide a flow of only said fresh air to wash said oxygen fuel cell.

6. An anesthesia system as defined in claim 5 wherein said control means to control said flow of each of said gases comprises a central processing unit.

7. An anesthesia system as defined in claim 6 wherein said means to generate a signal indicating the termination of the use of the anesthesia system on a patient comprises an input device operable by the user.

8. An anesthesia system as defined in claim 6 wherein said plurality of gases include oxygen, nitrous oxide and an anesthetic agent.

9. An anesthesia system as defined in claim 8 wherein said anesthesia system further includes an anesthetic agent sensor in said patient circuit for detecting the concentration of anesthetic agent in said patient circuit and said sensor provides a signal to said central processing unit to terminate the flow of air when said anesthetic agent sensor detects the reduction of the concentration of anesthetic agent in said patient circuit to a predetermined concentration.

10. A method of providing air wash of an anesthesia system comprising;

(a) providing a patient circuit for connection to a patient to introduce gases into the patient and to receive gases from the patient;

(b) providing a flow of a plurality of gases to the patient circuit, including at least oxygen and fresh air;

(c) providing an oxygen fuel cell in said patient circuit to monitor the concentration of oxygen in the patient circuit and to generate a signal indicative of that oxygen concentration;

(d) generating a signal indicative of the termination of the operation on a patient, (e) increasing the flow of air into the patent circuit in response to the signal generated in step (d) while terminating the flow of oxygen and any other of said plurality of gases to wash the patient circuit including said oxygen fuel cell with only fresh air.

11. A method of providing air wash of an anesthesia system as defined in claim 10 further including the step of:

(f) terminating the increased flow of air of step (e) after a predetermined period of time.

12. A method of providing air wash of an anesthesia system as defined in claim 10 further including the step of;

(f) terminating the increased flow of air of step (e) upon the said sensing of step (c) determining that the oxygen concentration is reduced to a predetermined concentration.

13. A method of providing air wash of an anesthesia system as defined in claim 12 wherein said sensing of step (c) determines that the oxygen concentration is reduced to about 21 percent.

* * * * *